United States Patent
Chien

(10) Patent No.: US 7,045,145 B1
(45) Date of Patent: May 16, 2006

(54) TRANSDERMAL CONTRACEPTIVE DELIVERY SYSTEM AND PROCESS

(75) Inventor: Te-Yen Chien, Neshanic Station, NJ (US)

(73) Assignee: Agile Therapeutics, Inc., West Conshohocken, PA (US)

( * ) Notice: Subject to any disclaimer, the term of this patent is extended or adjusted under 35 U.S.C. 154(b) by 112 days.

(21) Appl. No.: 10/130,913

(22) PCT Filed: Nov. 22, 2000

(86) PCT No.: PCT/US00/32043

§ 371 (c)(1),
(2), (4) Date: May 23, 2002

(87) PCT Pub. No.: WO01/37770

PCT Pub. Date: May 31, 2001

Related U.S. Application Data

(60) Provisional application No. 60/167,535, filed on Nov. 24, 1999.

(51) Int. Cl.
*A61F 13/02* (2006.01)
*A61L 15/16* (2006.01)
(52) U.S. Cl. .................. 424/448; 424/449; 424/443
(58) Field of Classification Search ............. 424/448, 424/449, 443
See application file for complete search history.

(56) References Cited

U.S. PATENT DOCUMENTS

| 2,918,494 | A | 12/1959 | Closson ................... 260/541 |
| 2,964,546 | A | 12/1960 | Miwa et al. ............... 260/415 |
| 5,023,084 | A * | 6/1991 | Chien et al. .............. 424/448 |
| 5,296,230 | A | 3/1994 | Chien et al. .............. 424/448 |
| 5,560,922 | A | 10/1996 | Chien et al. .............. 424/448 |
| 5,567,922 | A | 10/1996 | Schmuck et al. ......... 181/284 |
| 5,686,097 | A | 11/1997 | Taskovich et al. ........ 424/448 |
| 5,702,956 | A | 12/1997 | Ying et al. ................... 437/8 |
| 5,762,956 | A | 6/1998 | Chien et al. .............. 424/449 |
| 5,788,983 | A | 8/1998 | Chien et al. .............. 424/449 |
| 5,876,746 | A | 3/1999 | Jona et al. ................ 424/449 |

FOREIGN PATENT DOCUMENTS

EP 1 242 012 9/2002

* cited by examiner

*Primary Examiner*—Thurman K. Page
*Assistant Examiner*—Isis Ghali
(74) *Attorney, Agent, or Firm*—Woodcock Washburn LLP

(57) ABSTRACT

A transdermal contraceptive delivery system (TCDS) for fertility control in women is described. It comprises a backing layer, an adjoining layer of a solid absorption adhesive polymer matrix in which effective daily doses of an estrogen and a progestin are dispersed and released for transdermal absorption. Presently preferred is the use of the synthetic estrogen, ethinyl estradiol, and the synthetic progestin, levonorgestrel. Along with these two steroidal contraceptive agents, a combination of several chemical skin permeation enhancing agents, including capric acid, blended at specific weight ratios, ranging from 2:1:1:0.8 to 6:1:1:0.8, are homogeneously dispersed in the adhesive polymer matrix. The invention also provides a method of fertility control utilizing the transdermal contraceptive delivery system.

34 Claims, 8 Drawing Sheets

TRANSDERMAL CONTRACEPTIVE DELIVERY SYSTEM AND PROCESS

Pursuant to 35 U.S.C §371, this is a national stage of International Application PCT/US00/32043, filed Nov. 22, 2000, which claims benefit under 35 U.S.C. 119(e) of U.S. Provisional Application Ser. No. 60/167,535, filed Nov. 24, 1999, the entire contents of which are incorporated by reference herein.

BACKGROUND OF THE INVENTION

This invention relates to a novel transdermal fertility control system for females and a process for controlling fertility. The system involves transdermal absorption dosage units adapted for adhesion to the female subject designed for fertility control or prevention of an unwanted pregnancy. Further, the invention relates to a method of controlling fertility by utilizing a transdermal system of applying a series of transdermal polymer matrix dosage units having dissolved or microdispersed in the matrix layer effective dosage amounts of an estrogen, preferably ethinyl estradiol and a progestin, preferably, levonorgestrel. The system is an improvement of the prior art because it has an improved delivery rate of levonorgestrel, which is typically impermeable to the skin. The improved delivery rate allows for a reduced skin permeation time of the active agents allowing high blood levels of the hormones to provide sufficient and adequate contraception. A reduced size of the transdermal patch can be utilized because of the improved delivery rate of levonorgestrel.

Typically, combinations of synthetic estrogen and synthetic progestin have been used in the past in orally administered dosage forms to control fertility. If a natural estrogen (17 beta estradiol) and progestin (progesterone) combination is to be used in the oral contraceptive pills, very large doses of these two hormones will be needed because of very extensive hepatic first-pass metabolism of the two hormones in the liver. The resulting metabolic products often cause undesired side effects. Therefore, a combination of synthetic progestin and estrogen are used to overcome the deficiencies.

Although the combination of synthetic progestin and estrogen is very effective in suppressing ovulation, certain undesirable side effects are still prevalent with this type of oral contraceptive. The incidence of thromboembolic and related vascular disorders, including stroke and myocardial infarction, is higher in women using oral contraceptives; the relative risk may be eleven times greater in users as compared to a control population. Further, the risk increases sharply in women over 35 years of age. Contraceptive use has also been associated with increased evidence of benign liver tumors and an increased risk of gallbladder disease. Additionally, fetal abnormalities may result if the mother continues to take the pill after becoming pregnant. Finally, some possible, but unproven complications of contraceptive use include breast cancer, and cancer of the uterus, cervix and vagina.

An ideal and patient-acceptable fertility control system should provide the following advantages: minimized side effects, increased ease of administration, rapid termination of treatment, and improved patient compliance. In recent years, considerable attention has been directed to the development of implantable, intrauterine, cervical or vaginal fertility control delivery systems to provide a prolonged and controlled administration of steroidal hormones to the body for achieving fertility control. However, none of the delivery systems developed so far can be considered ideal and free of side effects.

On the other hand, absorption of pharmaceuticals through the skin, i.e., transdermal drug delivery provides avoidance of many undesirable side effects. Specifically, transdermal rate-controlled drug administration provides: (i) avoidance of the risk and inconvenience of intravenous therapy and of the variability in absorption and metabolism associated with oral therapy; (ii) continuity of drug administration, permitting the use of a pharmacologically active agent with short biological half-life; (iii) efficacy can be achieved with lower total daily dosage of drug, since there is reduced degradation in the digestive system; (iv) less chance of over- or under-dosing; (v) provision of a simplified medication regimen; and (vi) ability to rapidly terminate the drug infusion, if needed, by removal of the drug delivery system from the skin surface.

It is, therefore, highly desired that transdermal systems be provided which permit 1) use of either synthetic or natural estrogen, 2) use of high levels of progestin, 3) use of a minimum number of dosage units for each menstrual cycle, and 4) that provide sufficiently high levels of estrogen and progestin hormones to provide high assurance of fertility control without a high amount of undesired metabolic or chemical degradative products.

In recent years various transdermal contraceptive delivery systems for fertility control in females have been developed.

U.S. Pat. No. 5,567,922 discloses the delivery of a natural estrogen, 17-beta estradiol, or ethinyl estradiol or a combination thereof with an amount of natural progestrogen or a progestin in a dosage unit comprising a backing layer and an adjoining polyacrylate adhesive polymer layer which releases the hormones.

U.S. Pat. No. 5,296,230 describes a transdermal fertility controlling polymer matrix dosage unit comprising a backing layer and a polymer matrix disc layer which is adhered to the backing layer comprising microdispersed dosage amounts of estrogen and progestin hormones, the polymer matrix disc layer having a surface of about 20 $cm^2$.

U.S. Pat. No. 5,788,983 discloses a transdermal polymer dosage unit, a backing layer and a reservoir layer, the reservoir layer having multiple regions which contact the skin during use and optionally contain different pharmaceutical therapeutic agents providing a variable rate of absorption.

U.S. Pat. No. 5,762,956 describes a transdermal contraceptive delivery device and a method of fertility control utilizing the device. The system comprises a backing layer, and an adhesive polymer matrix, which has dispersed therein hormones effective for controlling fertility, as well as a combination of skin permeation enchancers. The adhesive polymer matrix provides a site for where the hormones and skin permeation enhancers are dispersed but also serves to adhere the delivery system in intimate contact with the skin of the subject being treated to permit the hormones to be absorbed transdermally. Typically about 300 to 400 pg/ml of levonorgestrel are released into the blood stream within a suitable period of time. It has been found that this level of levonorgestrel released into the bloodstream by transdermal route for the indicated period of time may be insufficient for effective and safe fertility control.

The present invention is an improvement over the deficiencies of the prior art in that it provides high serum levels of levonorgestrel and a desired profile of levonorgestrel for contraception and a desired level and profile of ethinyl estradiol while maintaining minimal side effects.

SUMMARY OF THE INVENTION

The present invention is directed to an improved transdermal contraceptive delivery system (TCDS) and a method of fertility control utilizing the TCDS of the present invention. The system comprises a backing layer, and an adhesive polymer matrix which has dispersed therein hormones effective for controlling fertility, as well as an effective combination of skin permeation enhancers and adhesive polymer matrix to increase the rate of drug permeation through skin. As well as providing the matrix within which the hormones and skin permeation enhancers are dispersed, the adhesive polymer matrix also serves to adhere the delivery system in intimate contact with the skin of the subject being treated to permit the hormones to be absorbed transdermally. The specific types and amounts of skin permeation enhancers, adhesive polymer and plasticizer increase the hormone release rate, thereby reducing the skin release time providing a high rate of delivery of the hormones.

Preferably, the materials used for the backing layer are laminates of polymer films with or without a metal foil such as aluminum foil. It is further preferred that the backing layer will be a thickness of from about 10 to about 300 microns. Preferably, the thickness will be from about 20 to about 150 microns, and more preferably, will be from about 30 to about 100 microns.

It is preferred that the adhesive polymer matrix be fabricated from biologically acceptable adhesive polymers, such as polyacrylic adhesive polymers, silicone adhesive polymers or polyisobutylene adhesive polymers. Preferably, the adhesive polymer layer is fabricated from a polyacrylate adhesive. More preferably, the polyacrylate adhesive will be of the general formula:

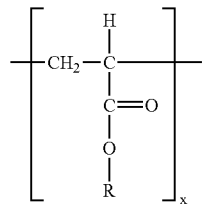

wherein x represents the number of repeating units sufficient to provide the desired properties in the polymer, and R is H or a lower ($C_1$–$C_{10}$) alkyl groups chosen from the group consisting of ethyl, butyl, and ethylhexyl. Most preferably, the adhesive polymer matrix of the present invention comprises a polyacrylate adhesive copolymer wherein, R is a 2-ethylhexyl group and the comonomer is vinyl acetate (about 3–60% w/w). The adhesive polymer matrix is solid and dimensionally stable, but is preferably thin, e.g. from about 10 to about 200 microns, preferably from about 20 to about 180 microns and most preferably from about 30 to about 150 microns in thickness.

It is preferred that the hormones utilized in the system of the present invention comprise an estrogen chosen from the group consisting of 17-beta estradiol, ethinyl estradiol and biocompatible derivatives thereof, and a progestin preferably, levonorgestrel or biocompatible derivatives thereof.

The adhesive polymer matrix of the present invention further comprises a moisture-regulating humectant/plasticizer or permeability modifier dispersed therein. Conventional humectant/plasticizers known in the pharmaceutical industry may be utilized. Preferably, the humectant/plasticizer will be a plasticizer. Most preferably it will be polyvinyl pyrrolidone/vinyl acetate, with a molecular weight of about 50,000. The inclusion of humectant/plasticizer serves to control the rigidity of the polymer matrix, as well as acting as a moisture regulating humectant. Incorporation of a humectant in the adhesive polymer matrix allows the TCDS to absorb moisture on the surface of skin, which in turn helps to reduce skin irritation and to prevent the TCDS from falling of during long-term (such as 7 days) use of the TCDS. The amount of humectant/plasticizer to be utilized will preferably be from about 0 to 10.0. More preferably, the amount of humectant/plasticizer utilized will be less than 5%, e.g., about 1.0% of the total adhesive polymer matrix.

The skin permeation enhancers utilized in the present invention consist of a combination of dimethyl sulfoxide (DMSO), a fatty alcohol ester of lactic acid and lower ($C_1$—$C_4$) aklyl ester of lactic acid. Preferably, the enhancer is a mixture of DMSO with lauryl lactate (available as Ceraphil 31 from Van Dyk Chem. Co., Belleville, N.J.), ethyl lactate and capric acid, a straight chain fatty acid. Capric acid has an empirical formula of $C_{10}H_{20}O_2$ and a molecular weight of 172. It is described in U.S. Pat. Nos. 2,918,494 and 2,964,546. Applicant has made the surprising discovery that the unique combination of skin permeation enhancers, especially including capric acid, with the adhesive polymer and plasticizer utilized in the present invention, when homogeneously dispersed in the adhesive polymer matrix at a particular ratio of about 2:0:1:1:0.8 to 6:1:1:0.8, preferably, 4:1:1:0.8, respectively, acts to solubilize the dispersed estrogen and progestin, thus greatly enhancing the amount of the dissolved hormones in the TCDS, which can result in greater skin permeation. Applicant has also discovered that the preferred skin permeation enhancer combination also enhances the tackiness and adhesion of the TCDS. The skin permeation mixture will be present in the adhesive polymer matrix in an effective amount of up to about 30% to about 60% w/w of the total matrix, and preferably at about 43% w/w of the matrix.

Optionally, an additional adhesive layer can be formed using the same or a different adhesive polymer which is also biocompatible and placed in intimate contact with the surface of the hormone-containing adhesive polymer layer. This adhesive layer can contain one or more effective transdermal absorption enhancing agents or be free of these agents.

The adhesive polymer layers can be formed by any acceptable method available to the art, such as spraying, solvent casting or laminating. The concentration of the skin permeation enhancers can be reduced in the portion of the adhesive polymer layer, as may be necessary if less than desired adhesion is realized, by applying the surface portion of the adhesive layer separately wherein the adhesive composition has a lower concentration of skin permeation enhancers.

The invention further provides a method of controlling fertility by applying a series of the transdermal contraceptive delivery systems to the skin of a subject to be treated, whereby said hormones contained therein are transdermally administered in an amount effective to prevent pregnancy.

DETAILED DESCRIPTION OF THE INVENTION

Figure 1:
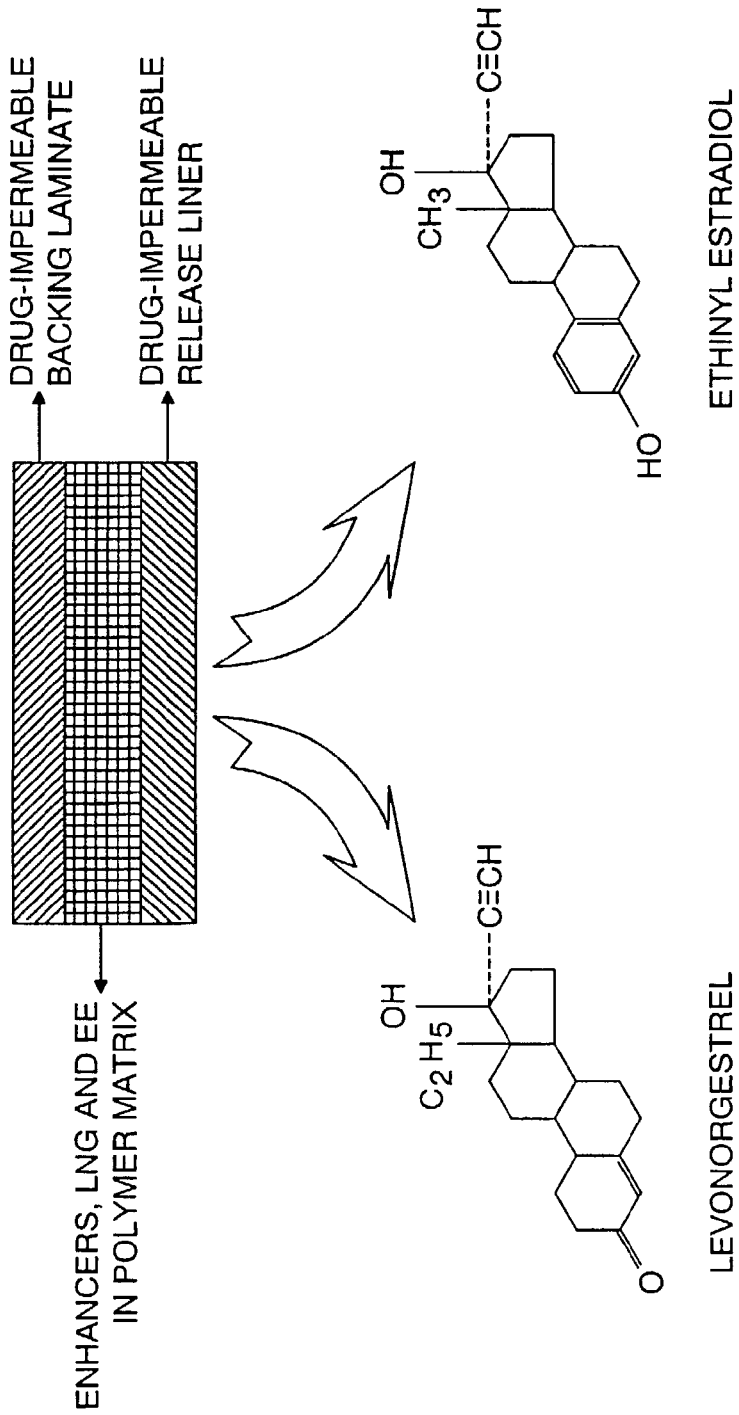
FIG. 1 is an illustration of the physical structure (side view) of the TCDS patch formulated and fabricated in Example 1.

The present invention is directed to a transdermal contraceptive delivery system (TCDS) comprising a backing layer and an adhesive polymer matrix which has dispersed therein hormones effective for controlling fertility as well as a combination of skin permeation enhancers and an adhesive polymer. It is an improvement over the transdermal contraceptive delivery system described in U.S. Pat. No. 5,762,956, the '956 patent' which is incorporated by reference. The '956 patent describes the use of the hormones, preferably 17-beta-estradiol and levonorgestrel dispersed in a solution comprising a polyol, such as polyethylene glycol and a combination of skin permeability enhancers, such as dimethyl sulfoxide, a fatty ($C_8$–$C_{20}$) alcohol ester of lactic acid, such as lauryl lactate (Ceraphil 31), a lower ($C_1$—$C_4$) aklyl ester of lactic acid, i.e. ethyl lactate. The skin permeation enhancers are typically present at a weight ratio of 2.5 to 5:1:1 to about 4:1:1. The total amount of the enhancer mixture can be up to about 10–60% w/w the polymer matrix. The humectant and/or plasticizer, polyethylene glycol, can be present in amounts from zero to about 24% based on the weight of the adhesive polymer matrix.

In making the TCDs of the '956 patent about one part of the total hormones are added to about 75 parts of the polyacrylate adhesive polymer in making the polymer matrix. The adhesive polymer is DURO TAK 87-4098. The transdermal delivery patch of the '956 patent was shown to deliver about 300 400 pg./ml of levonorgestrel, as measured in the bloodstream with a 20 cm$^2$ patch over a time period of 21 days.

The present invention provides an increased rate of hormone release thereby providing a high rate of delivery of the hormones. The levels of levonorgestrel exceed the level of 200–600 pg./ml needed for contraception and the 400 pg./ml levels achieved by the system described in the '956 patent. Indeed, levels of over 2000 (Cmax) pg./ml are reached with the system of the present invention when using a 10 cm$^2$ patch, which is a several fold increase over the levels shown in the '956 patent. Further, the levels of ethinyl estradiol range from about 35 to 75 pg/ml thereby providing effective contraception in women. The serum levels of hormones resulting from the present invention are obtained by using a relatively small patch, 7.5 to 12.5 cm$^2$ in an area, preferably 10 cm$^2$, which enhances the convenience of the user.

The Backing Layer

The backing layer can be made of any suitable material, which is impermeable to the hormones of the adhesive polymer matrix. The backing layer serves as a protective cover for the matrix layer and provides also a support function. The backing can be formed so that it is essentially the same size layer as the hormone-containing adhesive polymer matrix or it can be of larger dimension so that it can extend beyond the side of the adhesive polymer matrix or overlay the side or sides of the hormone-containing adhesive polymer matrix and then can extend outwardly in a manner that the surface of the extension of the backing layer can be the base for an adhesive means. For long-term applications, e.g., for seven days, it might be desirable to use microporous and/or breathable backing laminates, so hydration or maceration of the skin can be minimized.

Examples of materials suitable for making the backing layer are films of high and low density polyethylene, polyproplene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 300 microns. Preferably, the thickness will be from about 20 to about 15 microns, and more preferably, will be from about 30 to about 100 microns.

Adhesive Polymer Layer

Generally, those polymers used to form the biologically acceptable adhesive polymer layer are those capable of forming thin film or coatings through which hormones can pass at a controlled rate. Suitable polymers are biologically and pharmaceutically compatible, nonallergenic and insoluble in and compatible with body fluids or tissues with which the device is contacted. The use of insoluble polymers is to be avoided since dissolution or erosion of the matrix would affect the release rate of the hormones as well as the capability of the dosage unit to remain in place for convenience of removal.

Exemplary materials for fabricating the adhesive polymer layer include polyethylene, polypropylene, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylensilane copolymers), and the like; cellulose polymers, for example methyl or ethyl cellulose, hydroxypropyl methy cellulose, and cellulose esters; polycarbonates; polytetrafluoroethylene; and the like.

Preferably, the biologically acceptable adhesive polymer matrix should be selected from polymers with glass transition temperatures below room temperature. The polymer may, but need not necessarily, have a degree of crystallinity at room temperature. Cross-linking nonomeric units or sites can be incorporated into such polymers. For example, cross-linking monomers can be incorporated into polyacrylate polymers, which provide sites for cross-linking monomers for polyacrylate polymers include polymethacrylic estes of polyols such as butylene diacrylate and dimethacrylate, trimethylol propane trimethacrylate and the like. Other monomers which provide such sites include allyl acrylate, allyl methacrylate, diallyl maleate and the like.

Preferably, the adhesive polymer matrix comprises a polyacrylate adhesive polymer of the general formula (1):

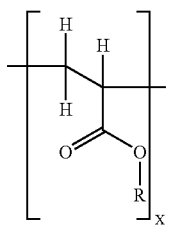

wherein x represents the number of repeating units sufficient to provide the desired properties in the adhesive polymer and R is H or a lower ($C_1$–$C_{10}$) alkyl, such as ethyl, butyl, 2-ethylhexyl, octyl, decyl and the like. More preferably, the adhesive polymer matrix comprises a polyacrylate adhesive copolymer which comprise a 2-ethylhexyl acrylate monomer and approximately 50–60% w/w/ of vinyl acetate as a comonomer. An example of a suitable polyacrylate adhesive copolymer for use in the present invention includes, but is not limited to, that sold under the tradename of DURO TAK 87-4098 by National Starch and Chemical Co., Bridgewater, N.J., which comprises a certain percentage of vinyl acetate comonomer.

A. Hormones

The specific hormones which may be dispersed in the adhesive polymer matrix include any hormones which are capable of controlling fertility and of being transdermally administered. With the controlled release of the hormone at a relatively steady rate over a prolonged period, typically several days and preferably one week, the subject is provided with the benefit of a steady infusion of he fertility-controlling amounts of hormones over a prolonged period. Preferably, the hormones utilized will actually be a combination of both a progestin component and an estrogen component.

It is presently preferred to use ethinyl estradiol. It is a synthetic hormone and ordinarily transdermally delivered by an adaptable system of this invention at a desirable daily rate while simultaneously a presently preferred progestin, the highly active levonorgestrel, is being transdermally absorbed at a desirably daily rate. Ethinyl and levonorgestrel are compatible and can be dispersed in the matrix layer-forming polymer. Conventionally, a transdermal dosage unit designed for one-week therapy is required to deliver at least about 20 mcg/day of levonorgestrel (or an equivalent effective amount of another progestin) and 10–50 mcg/day of ethinyl estradiol (or an equivalent effective amount of another estrogen). That amount of progestin is believed to be necessary to inhibit ovulation and that among of estrogen is believed needed to maintain normal female physiology and characteristics. In the present invention, the amount of levonorgestrel transdermally delivered is preferably 30 mcg. per day for more than one day to about one week with a 10 $cm^2$ transdermal delivery device rather than 20 mcg. per day. The ethinyl estradiol or equivalent is transdermally delivered at a rate of about 10 mcg. per day to about 50 mcg. per day.

Derivatives of 17-beta-estradiol which are biocompatible, capable of being absorbed transdermally and preferably bioconvertible to 17-beta-estradiol may also be used, if the amount of absorption meets the required daily dose of the estrogen component and if the hormone components are compatible. Such derivatives of estradiol include esters, either mono- or di-esters. The monoesters can be either 3- or 17-esters. The estradiol esters can be, illustratively speaking, estradiol-3, 17-diacetate; estradiol-3-acetate; estradiol-17-acetate; estradiol-3, 17-divalerate; estradiol-3 valerate; estradiol-17-valerate; 3-mono, 17-mono and 3,17-dipivilate esters; 3-mono, 17-mono and 3,17-dipropionate esters; 3-mono, 17-mono and 3,17-di-cyclopentyl-propionate esters; corresponding cypionate, heptanoate, benzoate and the like esters; ethinyl estradiol; estrone; and other estrogenic steroids and derivative thereof which are transdermally absorbable.

Combinations of the above or other with estradiol, for example, a combination of estradiol and estradiol-17-valerate or further a combination of estraldiol-17-valerate and estradiol-3, 17-divalerate can be used with beneficial results. For example, 15–80% of each compound based on the total weight of the estrogenic steroid component can be sued to obtain the desired result. Other combinations can also be used to obtain desired absorption and levels of 17-beta-estradiol in the body of the subject being treated.

The progestin hormone, as expressed above, is preferably levonorgestrel. Levonorgestrel is a potent progestin on a weight-dose basis, which is an important factor since the progestins often show a much lesser degree of transdermal absorption than by ethinyl estradiol and certain derivatives thereof. Other progestins which can be used in part or total are norgestrel, norgestinate, desogestrel, gestodene, norethindrone, nore-thynodrel, hydrogesterone, ethynodiol dicetate, hydroxyprogesterone caproate, medroxyprogesterone acetate, norethindrone acetate, progesterone, megestrol acetate, gestogen and certain others which are biocompatible, absorbable transdermally, including biocompatible derivatives of progestins which are transdermally absorbed, desirably such derivatives which are bioconvertible after transdermal absorption to the original progestin. The progestin and estrogen hormones should have high compatibility with each other.

It will be appreciated that the hormones may be employed not only in the form of the pure chemical compound, but also in admixture with other pharmaceuticals which may be transdermally applied or with other ingredients which are not incompatible with the desired objective of fertility control. Thus simple pharmacologically acceptable derivatives of the hormones such as ethers, esters, amides, acetals, salts and the like, if appropriate, may be used. In some cases, such derivatives may actually be preferred.

The progestin compound and the estrogenic steroid are ordinarily dispersed or dissolved concurrently in fabricating the hormone-containing adhesive polymer matrix or they may be dispersed or dissolved separately.

B. Humectant/Plasticizer

Preferably, a plasticizer/humectant or permeability enhancer is dispersed within the adhesive polymer matrix. The plasticizer/humectant may be a conventional plasticizer used in the pharmaceutical industry, for example, polyvinyl pyrrolidone. Preferably, polyvinyl pyrroliodone/vinyl acetate, such as those having a molecular weight of from about 50,000 can be used with the present invention. The polyvinyl pyrrolidone/vinyl acetate acts as both a plasticizer, acting to control the rigidity of the polymer matrix, as well as a humectant, acting to regulate moisture content of the formulation. Incorporation of a humectant in the formulation allows the dosage unit to absorb moisture on the surface of skin which in turn helps to reduce skin irritation and to prevent the adhesive polymer layer of the delivery system from failing. Preferably, the plasticizer and/or humectant is PVP/VA S-630 supplied by ISP International Specialty Products, Inc. of Wayne, N.J., wherein the PVP is present in an amount of about 60% weight and the vinyl acetate is present in an amount of about 50% by weight of the total mixture.

Depending upon the hormones utilized and the drug delivery desired, a suitable amount of a plasticizer can be varied from zero to about 10 percent (by weight) based on the weight of the adhesive polymer matrix. Preferably, the amount of humectant/plasticizer utilized is less than 5%.

The plasticizer can be added as an aqueous solution with the polyvinyl pyrrolidone/vinyl acetate contact varying from 1 to about 10 percent, based on the weight of the final dried matrix of the patch.

C. Skin Permeation Enhancers

Drug molecules released from a transdermal delivery system must be capable of penetrating each layer of skin. In order to increase the rate of permeation of drug molecules, a transdermal drug delivery system must be able in particular to increase the permeability of the outermost layer of skin, the stratum corneum, which provides the most resistance to the penetration of molecules. In this regard, this invention provides a transdermal contraceptive delivery system that employs a novel combination of skin permeation enhancers. It is this novel combination of skin permeation enhancers that provides the sufficient flux of the penetrating estrogen and progestin. The skin permeation enhances also provide the desired permeation rate ratio of these hormones to achieve the desired amount of estrogen and progestin to be released from the transdermal contraceptive delivery system and then delivered into the body to produce the desired contraceptive effect.

A combination of skin permeation enhancing agents is employed in the practice of the present invention which is a mixture of dimethyl sulfoxide (DMSO), a fatty ($C_8$–$C_{20}$) alcohol ester of lactic acid, such as lauryl lactate (Ceraphil 31), a lower ($C_1$–$C_4$) alkanol ester of lactic acid, i.e., ethyl lactate and capric acid. It is further preferred that these skin permeation enhancers be present at a weight ratio of 2.0:1:1:0.8 to 6:1:1:0.8, more preferably, about 4:1:1:0.8. The total amount of enhancer mixture can be up to about 10–60% w/w of the polymer matrix, preferably about 43% w/w when an acrylate copolymer is used.

Fabrication of TCDS Patches

In making the hormone-containing adhesive polymer matrix, polyacrylate adhesive polymers of the formula described hereinabove are preferably utilized. The hormones are added in an amount determined by the hormone dosage and the duration of treatment desired in each dosage unit. It has been found, for example, that one part total of hormones can be satisfactorily added to about 75 parts of the polyacrylate adhesive polymer utilized in making the polymer matrix.

Preferably, prior to mixing with polyacrylate adhesive polymer, the hormones used are dissolved and dispersed in a solution comprising a polyvinyl pyrrolidone/vinyl acetate and a combination of skin permeation enhancers. More preferably, the enhancer combination and the plasticizer solution are combined, the hormones added thereto and subjected to mixing. The amount of enhancers utilized depends in part on the rapidity at which the hormones are to be delivered. Generally speaking, it is preferred that about 10 to about 60 percent of skin permeation enhancer combination based on the weight of the adhesive polymer matrix solution is suitable. More preferably, about 40 to about 45 percent of skin permeation enhancer combination is used. It is preferred that the hormone-containing adhesive polymer matrix contain some excess of the dispersed hormone over the dosage amount desired to be delivered thereby. Preferably, the excess is about 5.0 to about 50 times the desired dosage. More preferably, the excess is about 10 to about 25 times the desired dosage to be transdermally absorbed.

The adhesive polymer solution is then preferably added to the solution of hormones dispersed in the enhancer combination/plasticizer (PVP/VA) solution. The mixture of the polyacrylate adhesive copolymer and the PVP/VA/enhancer/hormone solution is then thoroughly mixed using a high-torque mixer to form a homogeneous dispersion or solution of the hormones in the polyacrylate adhesive copolymer. The composition is then allowed to stand undisturbed until deaerated, i.e. for a time period of at least one hour up to 24 hours.

Once deaerated, the adhesive polymer matrix is preferably applied to a backing layer material, such as, for example, Scotch Pak 1109, 3M Co., St. Paul Minn., and subsequently dried at 60° C. for 15 minutes. The dried adhesive polymer matrix is then laminated with a piece of release liner (such as Scotch Pak 1012, 3M Co., St. Paul Minn.) of the same size to form a sheet of the transdermal contraceptive delivery systems. The resulting adhesive polymer matrix sheet can then be cut to form discs with desired shapes and sizes using a steel rule die and a hydraulic press. The discs generally should not exceed about 100 cm$^2$ in area. Preferably, the discs will be about 5 to 100 cm$^2$, more preferably, about 8 to about 80 cm$^2$. Most preferably, the discs will be about 10 to about 60 cm$^2$. A disc of 10 cm$^2$ is preferred because of its relatively small size, yet being capable of dispersing high levels of hormones. The shape of the discs can vary; they can be circular, square, rectangular or other desired shape. The resulting transdermal contraceptive delivery system unit dosage forms are then placed in appropriate packaging for storage, such as paper and/or foil pouches, until they are to be applied in transdermal treatment.

The invention will be further described by reference to the following detailed examples.

EXAMPLE 1

Formulation and Fabrication of TCDS Patches

The physical structure (side view) of the TCDS patch formulated and fabricated in this example is illustrated in FIG. 1.

A. Formulation

The starting solution, comprising a mixture of the ingredients prior to application or coating is shown in Table A.

Sufficient amounts of the ingredients of Table A are utilized to obtain the amounts of the finished composition in Table B. Table B shows the finished adhesive polymer matrix, which is coated and dried, of the TCDS patch formulation utilized in the present invention and in this experiment:

TABLE A

| Ingredients | Concentration (%) |
|---|---|
| Coating Solution | |
| Ethinyl Estradiol | 0.65 |
| Levonorgestrel | 1.16 |
| PVP/VA-S630 | 0.50 |
| Enhancer Combination | 43.00 |
| DURO TAK 87-4098 | 52.70 |

TABLE B

| Ingredients | Concentration(%) |
|---|---|
| Dried Matrix Composition | |
| Ethinyl estradiol | 0.31 |
| Levonorgestrel | 0.53 |
| PVP/VA S-630 | 1.21 |
| Enhancer Combination | 20.71 |
| DURO TAK 87-4098 | 77.18 |

The enhancer combination contains dimethyl sulfoxide (DMSO), CERAPHIL 31, and ethyl lactate and capric acid at the weight ratio of 4:1:1:0.8. CERAPHIL 31 is the trade name of lauryl lactate (2-hydroxy-propanoic acid, dodecyl ester) manufactured by Van Dyk, a division of Mallinckrodt, Inc. in Belleville, N.J. Capric acid is available commercially from many sources. DURO TAK 87-4098 is the trade name of polyacrylate adhesive polymer solution manufactured by National Starch and Chemical Co., in Bridgewater, N.J. In the coating solution shown above, the ingredients are shown in preferred amounts for obtaining a dried finished matrix, however, the amounts are not intended to be limiting for they may be modified accordingly by a skilled worker in the art to yield a finished, dried matrix composition suitable for use. Sufficient amounts of the ingredients of the coating solution are utilized to achieve the results intended, and therefore may be varied by a skilled worker in the art. In the dried matrix composition, adjustments to the final weight to weight percentages can also be made by one skilled in the art and the product can still be effective. For example, the amount of the ethinyl estradiol and levonorgestrel can vary by plus or minus 5% w/w, the amount of PVP/VA S-630 may vary from 0 to about 10% w/w, the amount of the combination of skin permeation enhancers may vary from about 10% to about 60% w/w and the amount of the DURO TAK 87-4098, which is the amount needed to reach a total of 100% for all ingredients, may range from about 30% to about 60% w/w.

B. Fabrication Processes

The TCDS patches having the formulation described above were fabricated as follows. The hormones were weighed and put in a glass bottle. The other excipients were added and the bottle is shaken by hand until both hormones and PVP/VA-S630 are dissolved. The DURO TAK 87-4098 (33% solid content) adhesive polymer solution was added and the bottle was sealed. The contents of the bottle was stirred using the magnetic stirring bar at about 200 rpm at room temperature for 3 hours to form a homogeneous solution. The bottle was allowed to stand for at least one hour or until all air bubbles disappeared.

The resulting formulation was coated on a piece of backing laminate (Scotch Pak II 09, 3M Co., St. Paul, Minn.) to a thickness of 650 micrometers and subsequently dried at 60° C. for 15 minutes using a laboratory coating/drying machine (Model LTSV/LTH by Werner Mathis, Switzerland). After drying, the adhesive polymer matrix became approximately 100 micrometer thick.

The dried adhesive polymer matrix was laminated with a piece of release liner (Scotch Pak 1012, 3M co., St. Paul, Minn.) of the same size to form the sheet of TCDS. This sheet was cut into TCDS patches of 10 cm$^2$ using steel rule die and hydraulic press at 4000 psi. Each 10 cm$^2$ TCDS patch was individually packaged in a paper/foil pouch and stored in the refrigerator at a temperature of 4° C.

EXAMPLE 2

In-vitro Permeation Study

To confirm that the desired skin permeation rates of both ethinyl estradiol and levonorgestrel are achieved by the TCDS patch formulation described in Example 1, the patches manufactured were subjected to an in-vitro drug permeation study using human cadaver skin on the Valia-Chien side-by-side type skin permeation cell system (Crown Glass Co, Branchburg, N.J.). The samples taken from the receptor compartment of the diffusion cell were analyzed by high performance liquid chromatography.

Figure 2:
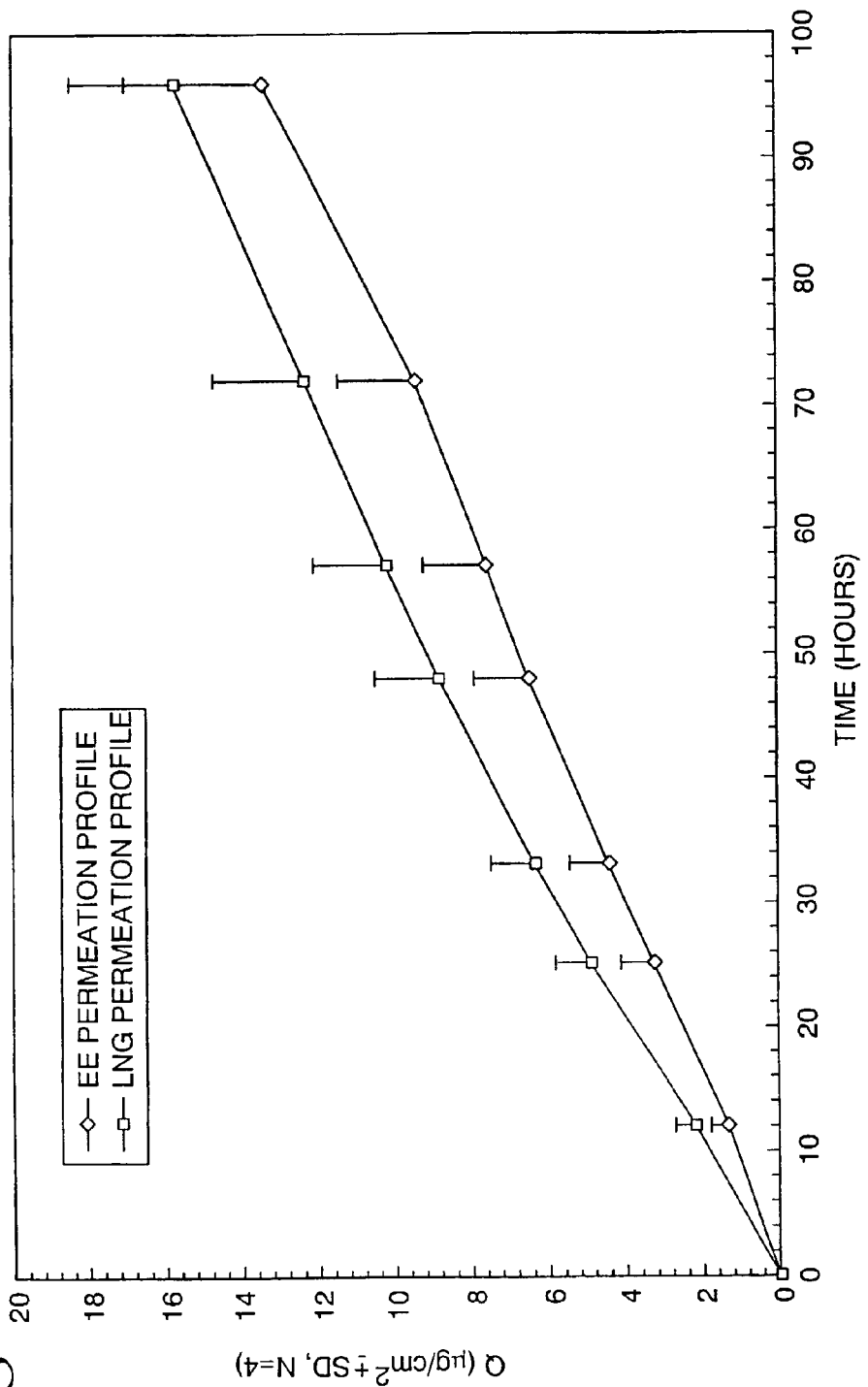
FIG. 2 is a graphical depiction of the in-vitro skin permeation profiles of both ethinyl estradiol and levonorgestrel as delivered from the TCDS patch formulation and tested on human cadaver skin.
Figure 3:
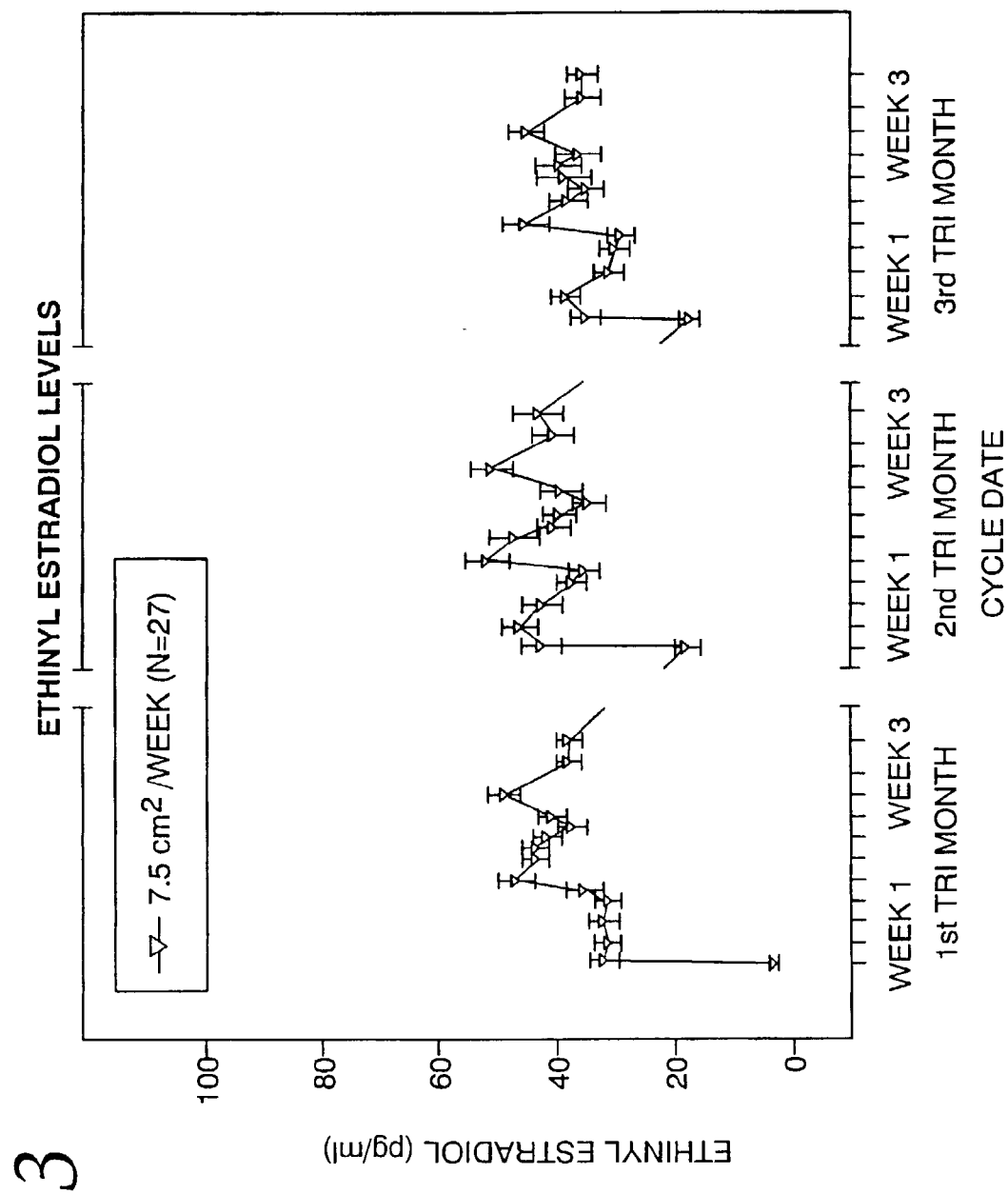
FIG. 3 is a graphical depiction of the serum profiles of ethinyl estradiol levels that resulted from the weekly application of one pieced of TCDS patch of 7.5 cm$^2$ to the subjects of Group A, B or C, respectively.

The in-vitro skin permeation profiles of both ethinyl estradiol and levonorgestrel were established and are shown in FIG. 2. The skin permeation flux of each drug was subsequently calculated from the steady state of the permeation profile. Based on the results of the in-vitro study, it was determined that about 60 mcg/day of levonorgestrel and 30 mcg/day of ethinyl estradiol were delivered from the 10 cm$^2$ TCDS patch fabricated in Example 1. The in-vitro skin permeation rates of levonorgestrel and ethinyl were estimated at 0.25 mcg/cm$^2$ hr and 0.13 mcg/cm$^2$ hr, respectively.

EXAMPLE 3

Dermal Toxicity Test

To investigate the potential of the developed TCDS patch formulation to cause skin sensitivity, a three-week dermal toxicity test was conducted. A total of forty-nine Hartley guinea pigs were used in the study. After the test there was an examination of each patch application. The patches of this TCDS formulation were tested on intact skin.

Skin Irritation and Sensitization Tests on Animal

A preliminary irritation study, followed by a Buehler sensitization test were conducted on the new TCDS formulation. The test article, TCDS patch, was evaluated for its potential to produce allergenic skin reactions following epicutaneous application to albino guinea pigs in comparison to a control patch (with and without enhancers), and a naïve untreated group. The TCDS patches tested were 1 cm$^2$ and 2 cm$^2$ which is estimated at 12.5–25.0 times the dosage of human by weight (0.4 kg for guinea pigs and 50 kg for human). The results of both skin irritation and sensitization tests showed that the TCDS patch formulation is not considered to be a skin sensitizer since none of the test animals exhibited erythema and edema scores at the challenge exposure following an induction phase in comparison to the control groups and the naïve untreated group. Significant reactivity (100%) was observed in the positive control group. The samples comprised the test article, a 1 cm² clear transdermal patch with levonorgestrel and ethinyl estradiol in acrylic adhesive matrix with enhancers. The control article was a clear transdermal patch, 1 cm² in size having the acrylic acetate matrix with or without enhancers. The positive control article was a patch having dinitrochlorobenyen (DNCB).

Preliminary Irritation Study

A Preliminary Irritation Study was performed with a total of nine (9) previously unexposed animals, divided into three groups, with three animals in each group. This phase was run before the start of the induction phase.

The group arrangement was 3 animals treated with either a one sq. cm patch, two sq. cum patch or non-active patch was applied (by the patch technique described below) to the skin for 6 six hours.

The responses were scored 24 and 48 hours after the test article application and the irritation potentials were determined.

The responses were scored 24 hours after the test article removal and the groups were ranked from lowest to highest irritations. The time of patch application (6 hours) as well as the treatment for the sensitization was determined from this irritation study. Since none of the animals exhibited any signs of irritation, the induction and challenge phases were conducted with both the test conditions and with an exposure period of 6 hours.

Induction Phase

Patches for the experimental group were prepared by applying the test article directly to the skin and covering with a gauze pad. The patch was kept in place with occlusive bandaging.

The patch was removed after exposure and any residual test article was removed gently with a pair of tweezers or scotch tape. Water was not used to wash off the residues.

The table below shows the treatment groups that were used in this sensitization study. Ten (10) female guinea pigs were utilized in each group for the induction and challenge with the test article. Five female animals were used in the positive control group, and in the untreated and negative control groups. The test article was applied once per week for 3 consecutive weeks (days, 0, 7, 14) on one side of the animal.

The positive control article dinitrochlorobenzene (DNCB), at a concentration of 0.4 ml or 0.1%, in acetone was applied in the same manner. Three control groups were utilized in this study.

TABLE C

| Group | Type of Patch |
|---|---|
| Control-1 | Patch & Adhesive (2 × 1 sq cm) |
| Control-2 | Patch & Adhesive & Enhancer (2 × 1 sq cm) |
| Test-1 | Dose 1 (1 sq cm) |
| Test-2 | Dose 2 (2 × 1 sq cm) |
| Untreated | — |
| Positive | DNCB |

Challenge (Day 28)

The day of the challenge, a 4×3 cm virgin skin site was shaved on the backs of the experimental and control animals.

During day 28, the challenge test was performed on freshly clipped skin sites the same as was the closed patch test of the induction phase. The skin was exposed to the test article for 6 hours. One virgin site was prepared per animal.

At 24±hours after removal of the challenge does, the area of the challenge was marked and the whole back shaved. At least two hours after shaving, the test site was examined for erythema and edema. Skin reactions were scored according to the four point scale described in Table 1.

Reading of the skin area was repeated 48±2 hours after the challenge and the skin reactions were graded.

The results were summarized and expressed in the following terms:

Incidence—The number of animals showing a response of 1 or more, at 24 or 48 hours, divided by the number of test animals.

Severity—The sum of the test grades divided by the number of animals tested.

No animals died during the course of the study. No therapeutic agents were used in any phase of the study. At the end of the study, all animals were sacrificed by Carbon dioxide ($CO_2$) inhalation.

Dosage

Preliminary Irritation

The test control articles were dosed and administered. Three animals each were exposed to either 1×1 sq. cm, 2×1 sq. cm or 2× non-active patches for a period of six hours.

Induction and Challenge Phase

The test and control articles were applied directly to skin at both induction and challenge. Twenty female animals were utilized for the test article. The naïve untreated animals were not induced.

During induction, the positive control article (0.4 mL of 0.1% DNCB in acetone) was applied in the same manner. For the challenge, the experimental animals were exposed to one does of the test article on day 28; the control animals were exposed to the control patches and 0.05% DNCB in acetone was used to challenge the positive control animals. Five animals were utilized for the untreated and control groups. Five animals were utilized for the positive control group.

Evaluation Data

The test article was graded according to the incidence and severity of observed responses, as described in Table 1.

TABLE 1

| | Value |
|---|---|
| Erythema and Eschar Formation | |
| No erythema | 0 |
| Very slight erythema (barely perceptible) | 1 |
| Well defined erythema | 2 |
| Moderate erythema | 3 |
| Severe erythema (beet redness) to slight eschar formation (injuries in depth) | 4 |
| Total possible erythema score = | 4 |
| Edema Formation | |
| No edema | 0 |
| Very slight edema | 1 |
| Slight edema (edges are well defined by definite raising) | 2 |
| Moderate edema (raised approximately 1 mm) | 3 |
| Severe edema (raised more than 1 mm and extending beyond area of exposure) | 4 |
| Total possible edema score = | 4 |

Results

Preliminary Irritation Trial

Irritation (erythema and edema) was absent from all sits treated with the test article, and the control groups.

Clinical Observations

No overt signs of toxicity were evident in any of the animals during the course of the study.

Induction Phase

No sign of erythema or edema were present in the test or control animals throughout the induction scoring phase. Two animals in the positive control group exhibited signs of erythema and edema following the second induction application. The untreated group was not induced. The results are shown in Table 2.

TABLE 2

Animal Species: Albino Guinea Pig

| | | | Induction Phase | | | Week 5 Challenge Phase | |
|---|---|---|---|---|---|---|---|
| Animal # | Sex | Group | Week 1* 10/29/98 | Week 2* 11/05/98 | Week 3* 11/12/98 | 24 hr* 11/27/98 | 48 hr** 11/28/98 |
| 1 | Female | Test 1 | 0/0 | 0/0 | 0/0 | 0/0 | 0/0 |
| 2 | Female | Dose 1 (1 sq. | 0/0 | 0/0 | 0/0 | 0/0 | 0/0 |
| 3 | Female | cm) | 0/0 | 0/0 | 0/0 | 0/0 | 0/0 |
| 4 | Female | | 0/0 | 0/0 | 0/0 | 0/0 | 0/0 |
| 5 | Female | | 0/0 | 0/0 | 0/0 | 0/0 | 0/0 |
| 6 | Female | | 0/0 | 0/0 | 0/0 | 0/0 | 0/0 |
| 7 | Female | | 0/0 | 0/0 | 0/0 | 0/0 | 0/0 |
| 8 | Female | | 0/0 | 0/0 | 0/0 | 0/0 | 0/0 |
| 9 | Female | | 0/0 | 0/0 | 0/0 | 0/0 | 0/0 |
| 10 | Female | | 0/0 | 0/0 | 0/0 | 0/0 | 0/0 |
| 11 | Female | Test 2 | 0/0 | 0/0 | 0/0 | 0/0 | 0/0 |
| 12 | Female | Dose 2 (2 × 1 | 0/0 | 0/0 | 0/0 | 0/0 | 0/0 |
| 13 | Female | sq. cm) | 0/0 | 0/0 | 0/0 | 0/0 | 0/0 |
| 14 | Female | | 0/0 | 0/0 | 0/0 | 0/0 | 0/0 |
| 15 | Female | | 0/0 | 0/0 | 0/0 | 0/0 | 0/0 |
| 16 | Female | | 0/0 | 0/0 | 0/0 | 0/0 | 0/0 |
| 17 | Female | | 0/0 | 0/0 | 0/0 | 0/0 | 0/0 |
| 18 | Female | | 0/0 | 0/0 | 0/0 | 0/0 | 0/0 |
| 19 | Female | | 0/0 | 0/0 | 0/0 | 0/0 | 0/0 |
| 20 | Female | | 0/0 | 0/0 | 0/0 | 0/0 | 0/0 |

*Observations directly after test article removal.
**Observations at 24 ± 2 and 48 ± 2 hours after test article removal Challenge Phase No signs of erythema or edema were observed in any of the test animals or the control groups. No signs of erythema or edema were evident in the untreated group. The animals in the positive control group exhibited signs of erythema and/or edema. The results are shown in Table 3.

TABLE 3

Animal Species: Albino Guinea Pig

| | | | Induction Phase | | | Week 5 Challenge Phase | |
|---|---|---|---|---|---|---|---|
| Animal # | Sex | Group | Week 1* Oct. 29, 1998 | Week 2* Nov. 5, 1998 | Week 3* Nov. 12, 1998 | 24 hr** Nov. 27, 1998 | 48 hr** Nov. 28, 1998 |
| 21 | Female | Control 1 | 0/0 | 0/0 | 0/0 | 0/0 | 0/0 |
| 22 | Female | Patch & | 0/0 | 0/0 | 0/0 | 0/0 | 0/0 |
| 23 | Female | Adhesive | 0/0 | 0/0 | 0/0 | 0/0 | 0/0 |
| 24 | Female | (2 × 1 sq. cm) | 0/0 | 0/0 | 0/0 | 0/0 | 0/0 |
| 25 | Female | | 0/0 | 0/0 | 0/0 | 0/0 | 0/0 |
| 26 | Female | Control 2 | 0/0 | 0/0 | 0/0 | 0/0 | 0/0 |
| 27 | Female | Patch & | 0/0 | 0/0 | 0/0 | 0/0 | 0/0 |
| 28 | Female | Adhesive & | 0/0 | 0/0 | 0/0 | 0/0 | 0/0 |
| 29 | Female | Enhancer | 0/0 | 0/0 | 0/0 | 0/0 | 0/0 |
| 30 | Female | (2 × 1 sq. cm) | 0/0 | 0/0 | 0/0 | 0/0 | 0/0 |
| 31 | Female | Untreated*** | — | — | — | 0/0 | 0/0 |
| 32 | Female | | — | — | — | 0/0 | 0/0 |
| 33 | Female | | — | — | — | 0/0 | 0/0 |
| 34 | Female | | — | — | — | 0/0 | 0/0 |
| 35 | Female | | — | — | — | 0/0 | 0/0 |

TABLE 3-continued

Animal Species: Albino Guinea Pig

| | | | Induction Phase | | | Week 5 Challenge Phase | |
|---|---|---|---|---|---|---|---|
| Animal # | Sex | Group | Week 1* Oct. 29, 1998 | Week 2* Nov. 5, 1998 | Week 3* Nov. 12, 1998 | 24 hr** Nov. 27, 1998 | 48 hr** Nov. 28, 1998 |
| 36 | Female | Positive Control | 0/0 | 0/2 | 0/2 | 2/1 | 2/0 |
| 37 | Female | DNCB | 0/0 | 0/0 | 1/1 | 2/2 | 1/1 |
| 38 | Female | | 0/0 | 0/1 | 2/1 | 2/3 | 1/2 |
| 39 | Female | | 0/0 | 1/0 | 2/3 | 1/2 | 1/1 |
| 40 | Female | | 0/0 | 1/2 | 3/2 | 2/2 | 2/1 |

*Observations directly after test article removal.
**Observations at 24 ± 2 and 48 ± 2 hours after test article removal
***Untreated control animals not induced.

TABLE 4

| Treatment Month | | 7.5 cm² | 10.0 cm² | 12.5 cm² |
|---|---|---|---|---|
| Summary of Levonorgesterol AUC | | | | |
| 1 | Mean | 18389.66 | 28928.92 | 32548.35 |
| | Std Error | 1602.59 | 1553.92 | 1989.54 |
| | N | 27 | 29 | 31 |
| 2 | Mean | 23205.02 | 35906.76 | 46641.41 |
| | Std Error | 2160.21 | 2736.79 | 3739.50 |
| | N | 27 | 28 | 31 |
| 3 | Mean | 21094.22 | 41366.82 | 59036.02 |
| | Std Error | 2061.43 | 3855.48 | 6163.24 |
| | N | 26 | 29 | 31 |
| Summary of Ethinyl Estradiol AUC | | | | |
| 1 | Mean | 802.29 | 1201.85 | 1304.24 |
| | Std Error | 35.35 | 68.92 | 63.56 |
| | N | 27 | 29 | 31 |
| 2 | Mean | 886.32 | 1184.84 | 1400.70 |
| | Std Error | 49.40 | 54.68 | 85.43 |
| | N | 27 | 28 | 31 |
| 3 | Mean | 784.59 | 1147.36 | 1455.50 |
| | Std Error | 52.81 | 80.56 | 100.68 |
| | N | 26 | 29 | 31 |

Serum level of levonorgestrel (LNG), ethinyl estradiol (EE) as well as luteinizing hormone (LH), progesterone (P) and estradiol (E2) were analyzed by radio-immunassay methods.

Ultrasound Measurements

Follicular size and endometrial thickness were measured by type-B ultrasound on each subjects for a total of 45 times (9 times per period) during the 5-month period of study at NRIFP.

Assessment of Contraceptive Efficacy

Since all the subjects were asked to use barrier-type contraceptive if they were engaged in sexual intercourse during the study, it is impossible to accurately assess the contraceptive efficacy of TCDS. However, the results of hormonal analysis and ultrasound measurements allowed the investigator to make an objective assessment of ovulation inhibition and implantation prevention which has been widely regarded as two possible mechanisms involved in the prevention of pregnancy for the woman taking contraceptive. It is also important to understand that other mechanism, such as the thickening of cervical/vaginal fluid, could play a major role in achieving the desired high contraceptive efficacy (greater than 99% theoretically) by the women who take contraceptive containing LNG.

Results

| A) Number of Subjects Completed the Study and Their Age Range | | | | | | | |
|---|---|---|---|---|---|---|---|
| | | | | | Age Range (years) | | |
| | completed | admitted | % completed | 21–25 | 26–30 | 31–35 | 36–40 |
| Group A | 26 | 42 | 62 | 1 | 3 | 9 | 13 |
| Group B | 29 | 41 | 71 | 2 | 9 | 8 | 10 |
| Group C | 31 | 41 | 76 | 4 | 3 | 8 | 16 |
| Total | 86 | 124 | 62 | 7 | 15 | 25 | 39 |

B) Body Weight Change

|  | No change | increase > 2 kg | decrease > 2 kg |
|---|---|---|---|
| Group A | 23 (88.5%) | 3(11.5%) | 0(0%) |
| Group B | 23 (79.0%) | 2(6.9%) | 4(13.8%) |
| Group C | 23 (74.0%) | 1(3.2%) | 7(22.6%) |

C) Side Effects

| Side Effect | No. of Subjects | | | Total (%) |
|---|---|---|---|---|
|  | Group A | Group B | Group C |  |
| Itching | 5 | 6 | 12 | 23 (26.7) |
| Reddish | 1 | 4 | 4 | 9 (10.5) |
| Sleepy Side Effect | 2 | 3 | 0 | 5 (5.8) |
| Dizziness | 1 | 2 | 2 | 5 (5.8) |
| Breast Engorgement | 0 | 2 | 1 | 3 (3.5) |
| Insomnia | 1 | 0 | 0 | 1 (1.2) |
| Nausea | 1 | 0 | 0 | 1 (1.2) |
| Appetite Change | 0 | 2 | 1 | 3 (3.5) |

With the exception of two subjects who suffered "moderate" itching and reddish, all of the side effects listed in the following are described as "mild" by the clinical investigator.

D) Spotting

Irregular and sporadic bleeding is a common phenomena for woman who began taking contraceptive that contains steroid hormonal drugs. This phenomena, in the case of oral pills, will gradually decrease after three months. The following table summarizes the results of spotting for woman who participated in this clinical study using the new TCDS patches.

| | Number (percentage) of subjects | | |
|---|---|---|---|
|  | T-1 | T-2 | T-3 |
| Group A | 10 (38.5) | 8 (30.8) | 6(23.0) |
| Group B | 14 (48.3) | 12 (41.4) | 4(24.1) |
| Group C | 14 (45.2) | 8 (25.8) | 6(19.4) |

The results of this spotting observation suggests that new TCDS patch formulation, like oral pills, cause higher percentage of spotting at the beginning and the spotting phenomena gradually decreases from month 1 to month 3 of the study. The percentage of woman experiencing the spotting also decrease with increasing dosage (from 7.5 cm$^2$/week to 12.5 cm$^2$/week). As compared to the percentage of woman who used the previous TCDS patch, (which has about 70% of spotting), the new TCDS formulation represents a big improvement.

E) Ultrasound Measurement

The results of ultrasound measurement on the follicular size and endometrial thickness of subjects that show the possibility of getting pregnant are summarized in the following table:

| | Number (percentage) of subjects | | | | | | | |
|---|---|---|---|---|---|---|---|---|
| | Baseline | | | | | | Recovery | |
| | Ovu | N.O. | L. | T-1 | T-2 | T-3 | Ovu. | N.O. | L. |
| Group A | 24(92.3) | 0 | 2 | 5(19.2) | 4(15.4) | 2(7.7) | 19(76) | 6 | 1 |
| Group B | 27(93.1) | 2 | 0 | 1(3.4) | 3(10.3) | 3(10.3) | 25(86) | 4 | 0 |
| Group C | 29(93.5) | 1 | 1 | 1(3.2) | 1(3.2) | 2(6.4) | 27(97) | 4 | 0 |

In order for pregnancy to occur, a subject must have both follicular size>16×16 mm and endometrial thickness 0.7 mm.

F) Serum Profiles of LNG and EE

FIGS. 3 through 8 show the serum levels of LNG and EE in each treatment groups. The levels of LNG achieved by this new TCDS formulation exceeded the level (200–600 pg/ml) that is considered necessary for effective contraception in women. Additionally, the levels of LNG achieved by TCDS formulation of the present invention are much higher than those achieved by the previous TCDS formulation of the '956 patent (at least about 400 pg/ml). By comparing the maximum mean serum concentration and area under the curve (AUC) of levonorgestrel during the first cycle of the clinical study, the new formulation shows 7.1 and 7.6 times of improvement, respectively, over the old formulation.

Figure 4:
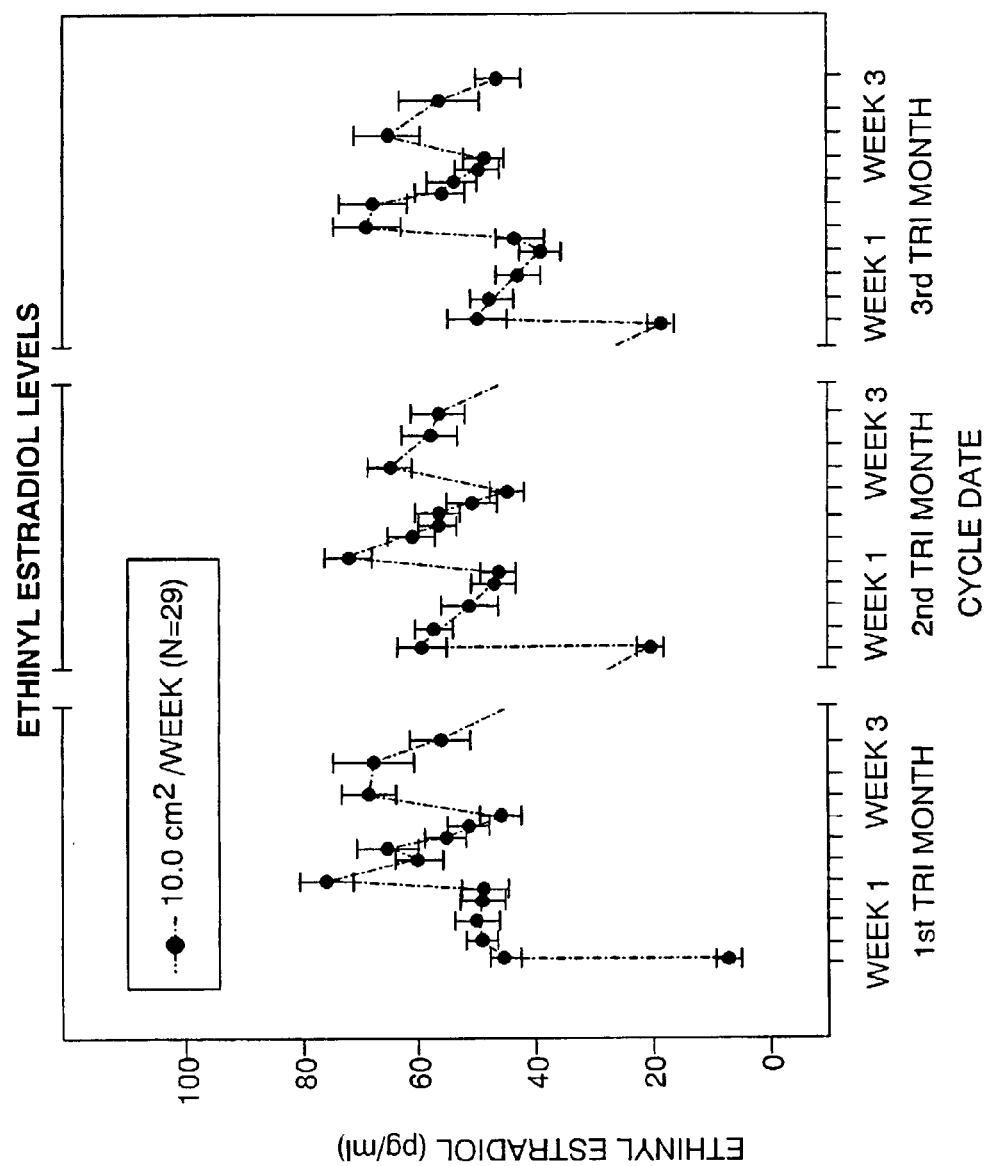
FIG. 4 is a graphical depiction of the serum profiles of ethinyl estradiol levels that resulted from the weekly application of one piece of TCDS patch of 10 cm$^2$ to the subjects of Group A, B, or C, respectively.
Figure 5:
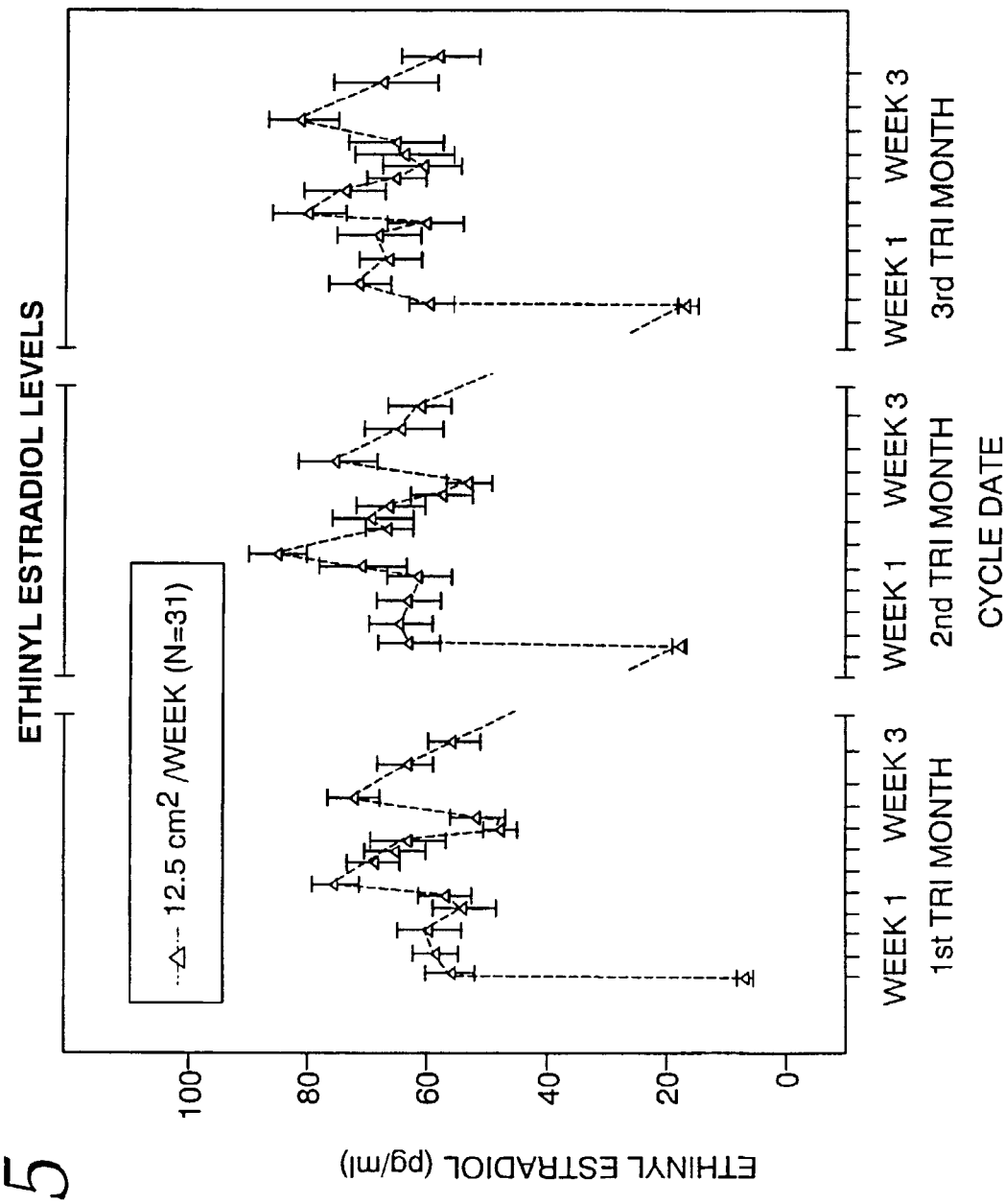
FIG. 5 is a graphical depiction of the serum profiles of ethinyl estradiol levels that resulted from the weekly application of one piece of TCDS patch of 12.5 cm$^2$ to the subjects of Group A, B or C, respectively.
Figure 6:
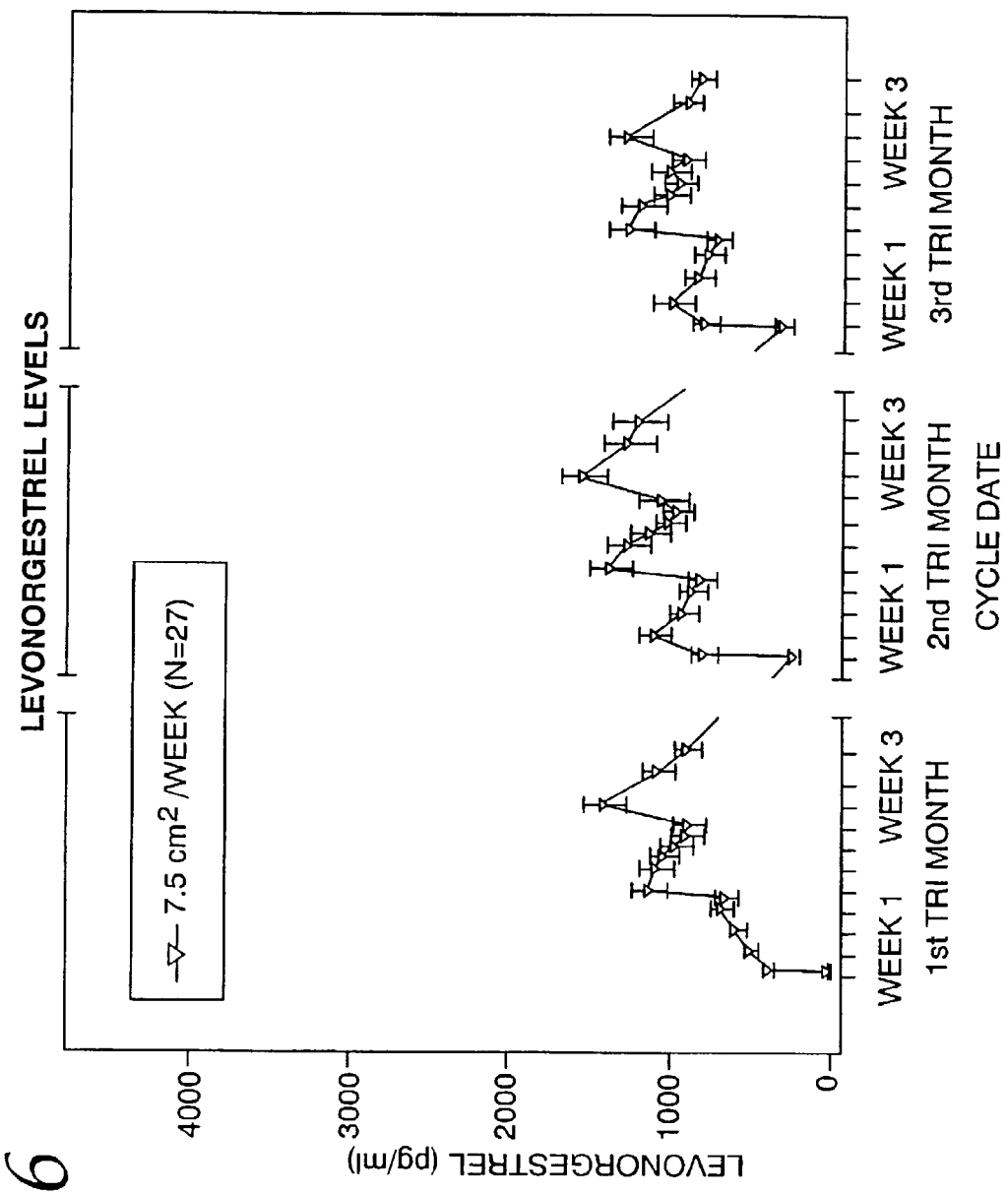
FIG. 6 is a graphical depiction of the serum profiles of levonorgestrel that resulted from the weekly application of one piece of TCDS patch of 7.5 cm$^2$ to the subjects of Group A, B or C, respectively.
Figure 7:
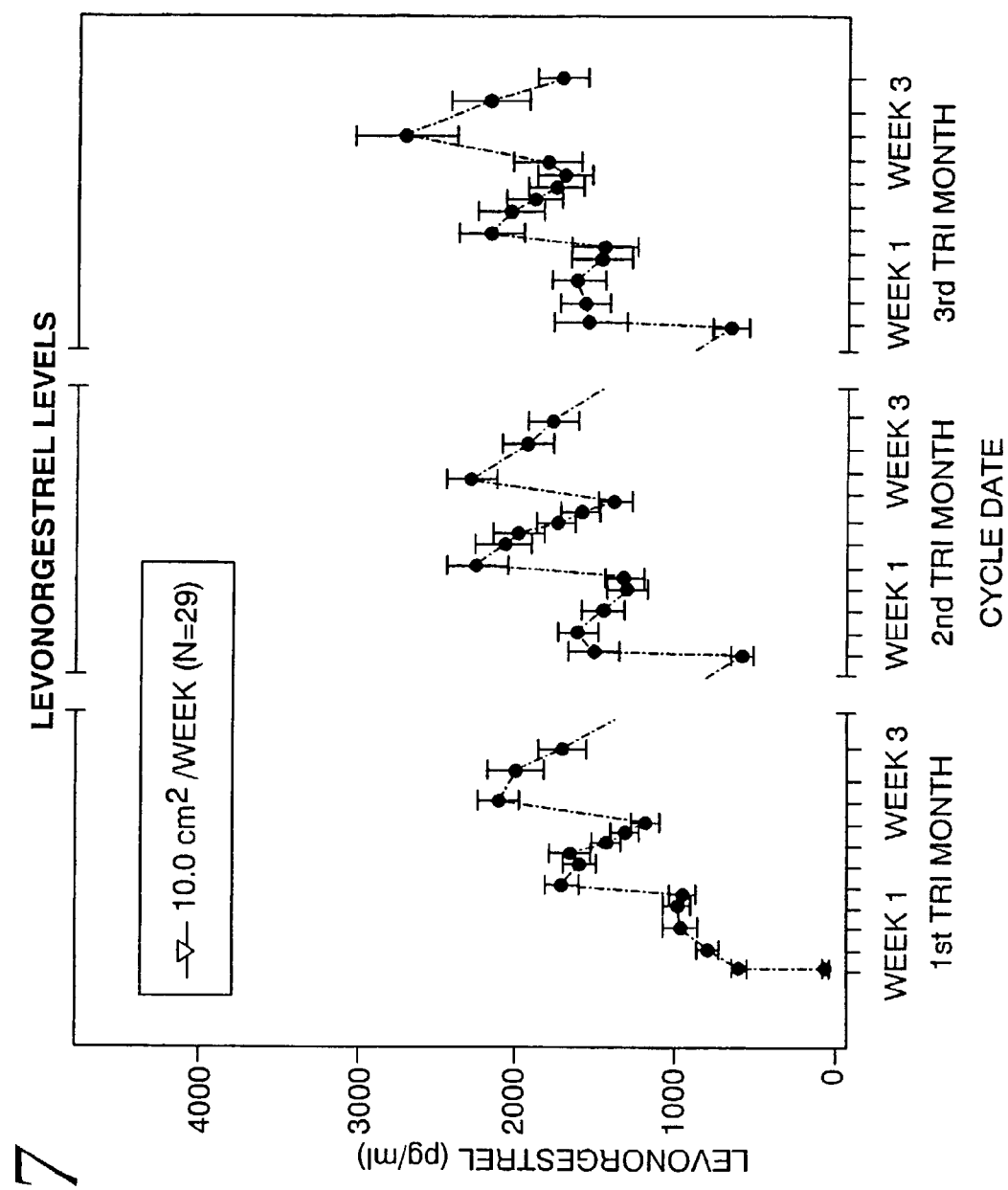
FIG. 7 is a graphical depiction of the serum profiles of levonorgestrel that resulted from the weekly application of one piece of TCDS patch of 10 cm$^2$ to the subjects of Group A, B or C, respectively.
Figure 8:
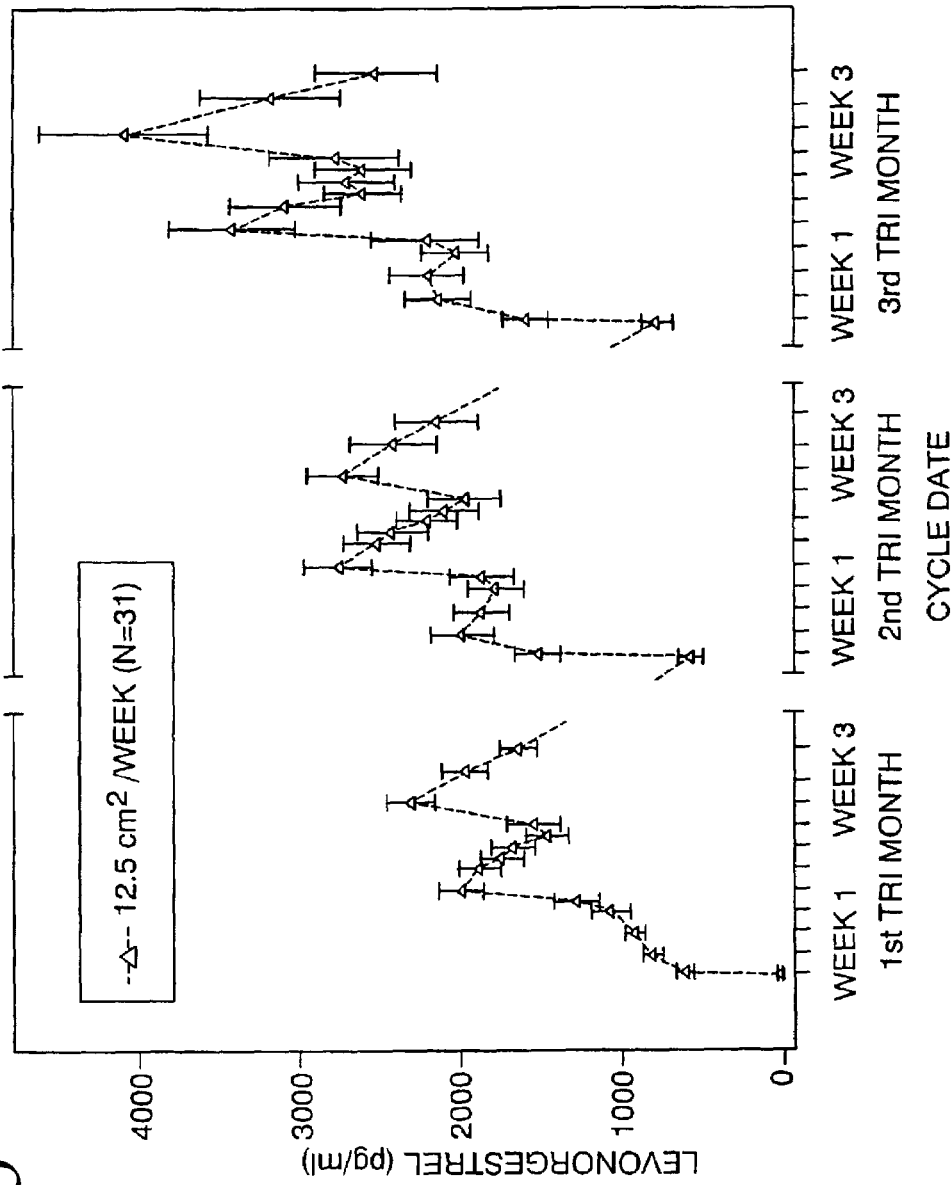
FIG. 8 is a graphical depiction of the serum profiles of levonorgestrel that resulted from the weekly application of one piece of TCDS patch of 12.5 cm$^2$ to the subjects of Group A, B or C, respectively.

FIG. 4 of the '956 patent shows the LNG levels for three groups, A,B, and C in a one month study. The subjects of Group A used patches having a diameter of 10 cm$^2$. The results are compared with levels of LNG shown for the first month of the study which results are shown in FIG. 7.

| TCDS Formulation | Cmax (pg/ml) | AUC(pg.day/ml) |
|---|---|---|
| New formulation (n = 29) | 2091.9 ± 130.8 (n = 29) | 28929.9 ± 1853.99 |
| Old formulation | 294.1 ± 77.7 (n = 8) | 3810.3 ± 2182.1 (n = 8) |

Improvement Ratio 7.1 7.6

The levels of EE achieved by the TCDS formulation of the present invention range from 35 to 75 pg/ml which is in the range that is desirable for a contraceptive regimen.

The area under the curve (AUC, in the unit of pg.day/ml) of both LNG and EE in each treatment group is summarized in Table 3. From these AUC's, the new TCDS formulation has achieved very high bioavailability in the users during this clinical study.

All patents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

EXAMPLE 4

Clinical Study

The total duration of study for each subject participating in this study is 5 months. It consists of one base-line period followed by three treatment periods and one recovery period. Each period is one menstrual cycle of the woman subjects.

Study Design

More than 130 Chinese woman of child-bearing age were recruited, screened (based on the inclusion/exclusion criteria), and 124 of them were admitted in this study.

Subjects attending this 5 month-long study were randomly divided and sequentially admitted into three study groups. Group A, B and C subjects received one piece of 7.5 cm$^2$, 10.0 cm$^2$ and 12.5 cm$^2$ TCDS patch weekly, respectively, for three consecutive weeks I each of the three treatment periods. During the baseline and recovery periods, all the subjects received only the placebo patch of the corresponding size for three consecutive weeks. During the fourth week of each study period, no patch was worn by the subjects in any treatment groups.

Blood Sampling

According to the blood sampling schedule, a total of 57 blood samples (about 10 ml per sample) were taken from each subject during the 5-month study. During the three treatment cycles, 15 samples were taken through out the 21 days of patch wearing period. At the end of the third treatment cycle, 5 additional blood samples were taken during the 24 hours post patch removal which allows the elimination pharmacokinetics of drugs to be studied. Serum samples were kept frozen in the freezer before they were subjected to analysis for their drug and hormonal levels.

Hormonal Analysis

What is claimed is:

1. A transdermal delivery system comprising a backing layer, and an adhesive polymer matrix affixed to the backing layer, wherein the adhesive polymer matrix is formulated by combining, on a weight percentage basis:
   a) from about 0% to about 10% of a humectant/plasticizer;
   b) from about 20% to about 70% of an adhesive copolymer;
   c) from about 10% to about 60% percent of a combination of skin permeation enhancing agents which is a mixture comprising dimethyl sulfoxide, a fatty ($C_8$–$C_{20}$) alcohol ester of lactic acid, a lower ($C_1$–$C_4$) alkyl ester of lactic acid and capric acid present in ratio ranging from about 2:1:1:0.8 to about 6:1:1:0.8, respectively;
   d) a progestin hormone; and
   e) an estrogen hormone.

2. The transdermal delivery system of claim 1, wherein the progestin is levonorgestrel.

3. The transdermal delivery system of claim 1, wherein the estrogen is selected from the group consisting of ethinyl estradiol and 17 β-estradiol.

4. The transdermal delivery system of claim 1, wherein the humectant/plasticizer is a polyvinylpyrrolidone/vinyl acetate.

5. The transdermal delivery system of claim 4, wherein the polyvinylpyrrolidone is formulated in an amount of about 60% w/w and the vinyl acetate is formulated in an amount of about 40% w/w in the polyvinylpyrrolidone/vinyl acetate mixture.

6. The transdermal delivery system of claim 1, wherein the adhesive copolymer comprises a polyacrylate copolymer.

7. The transdermal delivery system of claim 6 wherein the polyacrylate copolymer comprises a 2-ethylhexyl acrylate monomer.

8. The transdermal delivery system of claim 7 wherein the polyacrylate copolymer further comprises about 3 to 60% w/w vinyl acetate.

9. The transdermal delivery system of claim 1 wherein the fatty alcohol ester of lactic acid is lauryl lactate.

10. The transdermal delivery system of claim 9 wherein the lower alkyl ester of lactic acid is ethyl lactate.

11. The transdermal delivery system of claim 10 wherein the dimethyl sulfoxide, lauryl lactate, ethyl lactate and capric acid are formulated in a ratio of between about 2:1:1:0.8 and 6:1:1:0.8, respectively.

12. The transdermal delivery system of claim 11 wherein the dimethyl sulfoxide, lauryl lactate, ethyl lactate and capric acid are formulated in a ratio of about 4:1:1:0.8, respectively.

13. The transdermal delivery system of claim 3, formulated for delivery of ethinyl estradiol and levonorgestrel, wherein the ethinyl estradiol is transdermally delivered at a rate of between about 10 μg and 50 μg per day for a term of about one day to about one week, and the levonorgestrel is transdermally delivered at a rate of at least 20 μg per day for a term of about one day to about one week.

14. The transdermal delivery system of claim 13, wherein the levonorgestrel is transdermally delivered at a rate of at least 30 μg per day for a term of about one day to about one week.

15. The transdermal delivery system of claim 13, wherein the levonorgestrel is transdermally delivered in an amount sufficient to produce a blood concentration of at least 1,000 pg/ml.

16. The transdermal delivery system of claim 1 wherein the adhesive polymer matrix has a cross-sectional dimension of from about 10 to 300 microns.

17. The transdermal delivery system of claim 1, wherein the adhesive polymer matrix has a maximum surface area of 12.5 cm$^2$.

18. A method of controlling fertility by applying to the skin of a subject desiring such treatment a transdermal delivery system comprising:
   a backing layer, and an adhesive polymer matrix affixed to the backing layer, wherein the adhesive polymer matrix is formulated by combining, on a weight percentage basis:
   a) from about 0% to about 10% of a humectant/plasticizer;
   b) from about 20% to about 70% of an adhesive copolymer;
   c) from about 10% to about 60% percent of a combination of skin permeation enhancing agents which is a mixture comprising dimethyl sulfoxide, a fatty ($C_8$–$C_{20}$) alcohol ester of lactic acid, a lower ($C_1$–$C_4$) alkyl ester of lactic acid and capric acid present in ratio ranging from about 2:1:1:0.8 to about 6:1:1:0.8, respectively; and
   d) an amount of one or more fertility controlling hormones comprising a progestin and an estrogen effective to deliver at least a minimum effective daily dose of the one or more hormones to effect fertility control for between about one and about 7 days;
   wherein the transdermal delivery system is replaced once each week for three of four successive weeks of a menstrual cycle, for successive menstrual cycles extending as fertility control is desired.

19. The method of claim 18, wherein the transdermal delivery system delivers levonorgestrel.

20. The method of claim 19, wherein the transdermal delivery system delivers an estrogen selected from the group consisting of ethinyl estradiol and 17 β-estradiol.

21. The method of claim 18, wherein the humectant/plasticizer in the transdermal delivery system is a polyvinylpyrrolidone/vinyl acetate.

22. The method of claim 21, wherein the polyvinylpyrrolidone is formulated in an amount of about 60% w/w and the vinyl acetate is formulated in an amount of about 40% w/w in the polyvinylpyrrolidone/vinyl acetate mixture.

23. The method of claim 18, wherein the adhesive copolymer in the transdermal delivery system comprises a polyacrylate copolymer.

24. The method of claim 23 wherein the polyacrylate copolymer comprises a 2-ethylhexyl acrylate monomer.

25. The method of claim 24 wherein the polyacrylate copolymer further comprises about 3 to 60% w/w vinyl acetate.

26. The method of claim 18 wherein the fatty alcohol ester of lactic acid in the transdermal delivery system is lauryl lactate.

27. The method of claim 26 wherein the lower alkyl ester of lactic acid in the transdermal delivery system is ethyl lactate.

28. The method of claim 27, wherein the dimethyl sulfoxide, lauryl lactate, ethyl lactate and capric acid in the transdermal delivery system are formulated in a ratio of between about 2:1:1:0.8 and 6:1:1:0.8, respectively.

29. The method of claim 28 wherein the dimethyl sulfoxide, lauryl lactate, ethyl lactate and capric acid in the transdermal delivery system are formulated in a ratio of about 4:1:1:0.8, respectively.

30. The method of claim 20, wherein the transdermal delivery system is formulated for delivery of ethinyl estradiol and levonorgestrel, wherein the ethinyl estradiol is transdermally delivered at a rate of between about 10 µg and 50 µg per day for a term of about one day to about one week, and the levonorgestrel is transdermally delivered at a rate of at least 20 µg per day for a term of about one day to about one week.

31. The method of claim 30, wherein the levonorgestrel is transdermally delivered at a rate of at least 30 µg per day for a term of about one day to about one week.

32. The method of claim 30, wherein the levonorgestrel is transdermally delivered in an amount sufficient to produce a blood concentration of at least 1,000 pg/ml.

33. The method of claim 18 wherein the adhesive polymer matrix in the transdermal delivery system has a cross-sectional dimension of from about 10 to 300 microns.

34. The method of claim 18, wherein the adhesive polymer matrix in the transdermal delivery system has a maximum surface area of 12.5 cm$^2$.

* * * * *